United States Patent [19]
Winston et al.

[11] Patent Number: 6,142,777
[45] Date of Patent: Nov. 7, 2000

[54] DISPOSABLE DENTAL MIRROR

[75] Inventors: Paul E. Winston, Scarsdale; Ronald B. Wasserman, New York, both of N.Y.; Kenneth J. Berk, Newton, Mass.; Fredrick M. Berk, Brookline, Mass.; Donald A. Berk, Newton, Mass.

[73] Assignee: Pulpdent Corporation

[21] Appl. No.: 09/289,521

[22] Filed: Apr. 9, 1999

[51] Int. Cl.[7] ....................................................... A61B 1/24
[52] U.S. Cl. .............................. 433/30; 600/240; 600/247
[58] Field of Search ......................... 433/30, 31; 600/240, 600/247, 248

[56] References Cited

U.S. PATENT DOCUMENTS

| | | | |
|---|---|---|---|
| 477,791 | 6/1892 | Andrews | 600/240 X |
| 539,076 | 5/1895 | McNaughton | 600/247 X |
| 548,817 | 10/1895 | Platt | 600/247 X |
| 2,653,597 | 9/1953 | Canan | 600/247 X |
| 4,512,635 | 4/1985 | Melde | 433/30 X |
| 5,906,487 | 5/1999 | Carr | 433/30 |

*Primary Examiner*—Nicholas D. Lucchesi
*Attorney, Agent, or Firm*—Lee & Hollander

[57] ABSTRACT

A disposable dental mirror and methods of making same. The mirror includes a long, thin, flat blade that provides both a handle and a mirror mount and has a reflective surface applied to one end thereof. The blade is made of a material which need not be sterilizable, such as wood or plastic. In a one embodiment, the reflective surface is made of a metallized film directly applied to one surface of the blade. In an alternate embodiment, a thin, flat piece of a rigid material is located between the blade and the reflective film to ensure flatness of the reflecting surface, thereby reducing distortion.

25 Claims, 2 Drawing Sheets

DISPOSABLE DENTAL MIRROR

FIELD OF THE INVENTION

This invention is related to small disposable mirrors suitable for use in dentistry.

BACKGROUND OF THE INVENTION

Dentists have long used small, handheld mirrors when performing dental procedures such as oral surgery and restorative dentistry. The stereotypical dental mirror has a stainless handle with a reflecting surface affixed at an angle on the end of the handle. The reflecting surface in such a mirror is usually provided by a conventional glass mirror.

Such mirrors have disadvantages. They are costly to manufacture. They have a high tendency to fog up due to the relatively large heat capacity and conductance of the glass and metal materials which results in the mirror tending to remain at room temperature and condensing moisture on its surface when a patient exhales. This type of dental mirror also requires sterilization between patients via chemical or thermal processes.

Additionally, although the material in these dental mirrors can withstand chemical and thermal sterilization, the interface between the mirror and the metal handle is susceptible to retaining germs which may occasionally survive the sterilization process. Even when sterilization of the mirror is successful, unsightly debris and grit may be trapped in the gap around the mirror, and can be difficult to remove.

For these and other reasons, disposable dental mirrors have become popular in recent years. Disposable mirrors may be discarded after use so sterilization is not needed and transmission of viable pathogens between patients is completely avoided. Since they do not need to be able to withstand sterilization procedures, they may be made with lighter weight materials resulting in less fatigue during use. Disposable mirrors are less costly, and a dentist does not have to be so concerned with avoiding small scratches or abrasions on the mirror surface since the mirror may be simply discarded if damaged. Thus, disposable mirrors may be placed more closely to the work being done and the drill or other tools which might damage the mirror, resulting in a better view.

Typically, disposable mirrors are similar in configuration to the conventional, non-disposable mirror described above, but are made with less expensive materials. Handles may be a plastic material which can be made in large quantities at low expense by injection molding or other modern manufacturing methods. The reflecting surface is most often provided by a glass mirror.

While currently available disposable mirrors are less expensive than non-disposable mirrors, reducing costs still further is an on-going challenge. For example, U.S. Pat. No. 3,829,199 shows a disposable dental mirror which has a non-disposable handle which snaps into a disposable mirror/retainer assembly, thus reducing the cost of the disposable portion.

The cost of disposable mirrors becomes an even more important factor with a new dental technique call air abrasive dentistry. In this procedure, the dental drill normally used to remove decayed tooth material is supplemented or replaced by a high velocity air stream containing particles which abrade away the decayed tooth portions. In such procedures, an inherent problem is that some of the abrasive particles will ricochet off the tooth and impact the mirror surface with sufficient velocity to etch and damage it. Mirrors used in such procedures can have a very short lifetime, depending on the location of the cavity, and can become unusable within a few seconds.

Glass dental mirror pose another dilemma. A front surface mirror is desirable in a dental mirror to reduce distortion resulting from the double reflections of a rear surface mirror and refraction as light passes through the glass layer of the mirror. Front surface glass mirrors are, however, very delicate and susceptible to scratching from even minor contact by a dental instrument or drill. As a result, dental mirrors are available in both front and rear surface types to meet these conflicting requirements. Another approach to this problem has been to make the reflecting surface from a highly polished metal surface. While this provides a front surface mirror that is more durable than a glass front surface mirror, it is more expensive to replace when the reflecting surface is inevitably damaged.

SUMMARY OF THE INVENTION

The dental mirror of the present invention includes a unique design in which a long, thin, flat blade provides both a handle and a mirror mount and has a reflective surface applied to one end thereof. The blade is made of a material which need not be sterilizable, such as wood or plastic. In one embodiment, the reflective surface is made of a metallized film directly applied to one surface of the blade. In an alternate embodiment, the blade is fabricated from wood, and a thin, flat piece of a rigid material is located between the wooden blade and the reflective film to ensure flatness of the reflecting surface, thereby reducing distortion.

The mirror of the present invention is very inexpensive to manufacture and allows for an oblong configuration for the reflecting surface, which is desirable. The mirror has a reduced tendency to fog up due to the low thermal conductivity and thermal capacity of the materials.

The present invention also has the advantages of a front surface mirror without the drawbacks. In the preferred construction, the metallized film is applied to the handle with the plastic material uppermost. The plastic layer thus provides protection for the reflecting metallization layer, yet due to the thinness of the plastic layer, the distortion produced by refraction and double reflections is negligible.

DESCRIPTION OF THE DRAWINGS

The advantages and operation of the present invention are more fully described in the following description of the preferred embodiment and by reference to the drawings, of which.

DESCRIPTION OF THE PREFERRED EMBODIMENT

Figure 1:
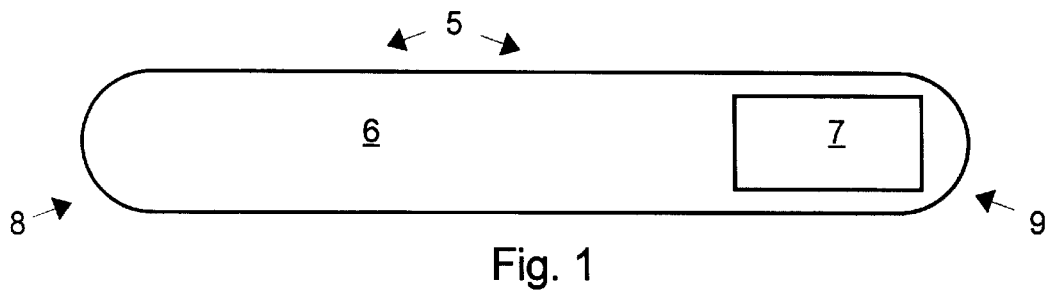
FIG. 1 shows a first embodiment of the invention.

FIG. 1 shows a first embodiment 5 of the disposable mirror of the present invention. In FIG. 1, an elongated, thin, flat blade 6 has at one end thereof a reflecting film 7 attached to its top surface. The blade 6 is preferably made of a strip of wood, similar to wooden tongue depressors used by physicians in oral examinations. Alternately the blade may be made of plastic or other materials.

The complete mirror thus includes a handle portion at the proximal end 8 thereof and a mirror at the distal end 9. This provides a disposable dental mirror that is inexpensive, light weight, and easy to use.

Figure 2:
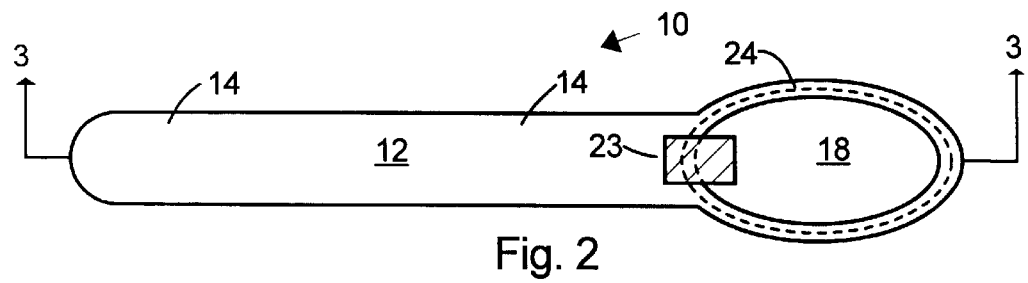
FIGS. 2 and 3 are top and sectional views respectively of a another embodiment of the present invention.
Figure 3:
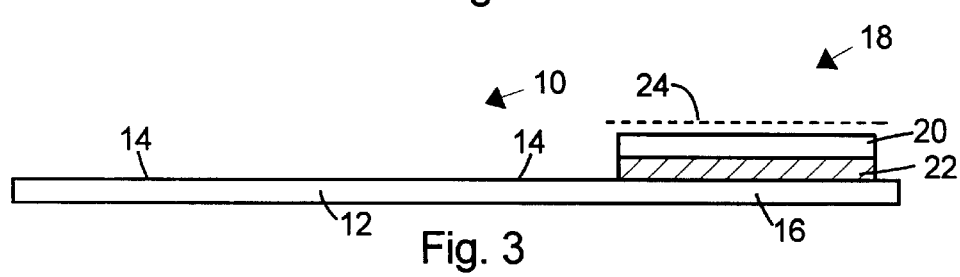

FIGS. 2 and 3 are top and side views respectively showing a second embodiment 10 of the disposable dental mirror of the present invention. In FIGS. 2 and 3, an elongated, thin, blade portion 12 provides a handle portion 14 at the proximal end thereof and a head portion 16 at the distal end. Blade 16 is preferably made of wood. Mounted to one surface of the head portion 16 is a reflecting film 18.

Handle portion 14 is narrower than the head 16 to provide a configuration easier to maneuver around teeth and gums in the mouth. The narrower handle also makes for easier manipulation by the user. In the embodiment shown in FIGS. 2 and 3, the handle portion 14 is preferably on the order of ⅜ to ½ inch wide, and the length of the blade 12, including both the handle and the head portions, is approximately 5½ inches. These dimensions, of course, may be made modified as required to suit individual preferences or to provide a smaller instrument, such as for use on a child. Additionally, the shape of the handle portion 14 may be varied from that shown, such as by tapering the handle along its length, for either aesthetic or functional reasons.

The head portion 16 of the blade 12 is wider than the handle portion 14. It serves to provide a substrate on which the reflecting material 18 is mounted. The head 16 may be made circular, to support a circular reflecting surface, but instead is preferably made elongate in the form of an oblong or oval with a similarly shaped reflecting film 18 mounted thereon, as shown in FIG. 2, one of the advantages of the present invention.

Conventional dental mirrors typically use circular glass mirrors, since such mirrors may be easily and inexpensively fabricated by a drilling operation using a hole saw to cut individual mirrors out of a larger mirrored piece of glass. Fabricating small, glass mirrors in shapes other than circular is difficult. Although dental mirrors come in a range of sizes, the most common sizes are ¾ to ⅞ inches in diameter.

In the disposable mirror shown in FIG. 2, the head 14 and the reflecting surface 18 are preferably about 1.3 inches long by 0.75 inches wide. The oval shape of the reflecting surface 18 is advantageous in many situations. It allows a mirror to show a larger extent of the teeth along the length of the mirror while not being so wide as to restrict manipulation of the mirror or being uncomfortable for the patient. For example, the 1.3 inch length of the mirror shown in FIGS. 2 and 3 allows a dentist to see four or five teeth in a typical adult. A circular mirror 1.3 inches in diameter would be very large and awkward to use, especially for procedures involving the molars in the back of the mouth.

Additionally, in air abrasive dentistry, the long reflecting surface of the present invention allows a dentist to slowly move the mirror along its lengthwise direction during the removal of decay. Thus, as part of the surface of the mirror is etched by ricocheting particles and becomes unusable, a new reflecting surface may be brought into place by merely moving the mirror along its length.

The reflecting surface 18 may be implemented by using a metallized, transparent, plastic film. This provides an inexpensive, lightweight mirror. In the described embodiment, the reflecting surface 18 is formed of plastic layer 20 having a metallized layer 22 formed on one surface thereof, as described in more detail below. The reflective film 18 is mounted to the surface of head portion 16 with a non-toxic adhesive, not shown in FIG. 3. Other thin, reflective, films may be used in place of the metallized plastic layer described herein, for example, the plastic material described in U.S. Pat. No. 3,711,176, which achieves high reflectivity in a thin sheet of plastic by using alternating layers of differing refractive index.

In the described embodiment, the film is mounted with the metallized layer 22 in contact with the blade 12. Although this technically provides a back surface mirror, the plastic layer 20 of the reflecting film 18 is sufficiently thin that there is no discernable distortion, and it has the advantage that the plastic layer 20 provides protection for the more delicate metallization layer 22. Thus, the present invention achieves the distortion-free reflection of a front surface mirror while providing protection for the metallization layer similar to a back surface mirror. Additionally, this construction protects the metallization layer from becoming tarnished or otherwise discolored. It should be appreciated that, although less desirable in most applications, the reflective film 18 may be attached to the blade 12 with the opposite orientation (i.e., with the plastic layer 20 attached to the blade and the metallization layer on top) while still achieving the other benefits of the present invention as described herein.

A removable, plastic, protective ply denoted by dotted lines 24 in FIG. 2, may optionally be applied to the top surface for protection. Such a ply prevents the plastic layer 20 from being scratched during packaging and shipment and allows the disposable mirrors to be packaged in bulk without requiring individual wrappers, thus further reducing costs. This protective ply also eliminates the aesthetic problem of dust accumulating on the surface of mirror 18 if it is exposed for a period of time before use. The protective ply 24 is concentric with the reflective film 18 and may be provided with a tab 23 to allow easy removal of the protective ply.

The mirror shown in FIGS. 2 and 3 and described above has been found to be an effective, inexpensive to produce, and otherwise highly suitable for use as a disposable dental mirror. Such a mirror may be inexpensively and efficiently manufactured in large quantities in the following manner.

The blades of the disposable mirrors may be manufactured in large quantities by punching out individual blades of the desired shape from a thin sheet of wood or plastic. The sheet from which the blades are cut is preferably 0.080 to 0.090 inch thick, although other thicknesses may be chosen. If made of wood, the blade should be made of a species of wood which has a low tendency to splinter of commonly available woods, birch has the best resistance to splintering and is a preferred material for fabricating the wooden blade 12.

It is important to eliminate edges anywhere on the disposable mirror 10 that might be capable of injuring oral tissues. Accordingly, prior to mounting the reflecting surface 18, the blade, if made of wood, should be tumbled together to round the corners and edges and eliminate any splinters. This procedure has been long used with wooden tongue depressors, and the safety record of such instruments is proof of its effectiveness. Additionally, the extreme thinness of the reflecting film 18 allows it to be mounted on one surface of the head portion 16 without the need for a protective molding around the edges of the film to prevent injury thereby.

When wood is used to make the blade portion of mirror 10, it has been found that over a period of time, and especially when stored in extreme environments of temperature or humidity, warpage of the wooden blade may cause a slight curve to develop in the blade along an axis parallel to the wood grain, which is normally the longitudinal axis of the mirror. This curve will result in a similar curve in the reflecting film 18, thereby producing a slightly distorted reflection. In some procedures, this distortion may be undesirable.

The tendency of a wooden blade to warp may be greatly reduced or eliminated by preventing moisture from being absorbed by the wood. Although a variety of methods may be used to achieve this, one especially simple and effective method is to add a hydrophobic material to the wooden blades during the above-described tumbling operation so that the wooden blade is coated or impregnated with the material during the tumbling operation. Carnauba wax is one suitable material which is non-toxic and effective to prevent warpage.

Tumbling the blade 12 with carnauba wax to prevent warpage can create a problem with the attachment of the reflecting film a 18 to the top surface of the blade, since many adhesives do not adhere well to the carnauba-impregnated wooden surface. It has been found that acrylic resin based adhesives are effective to attach the reflecting film 18 to a carnauba wax impregnated blade 12. In particular, Gelva® 737 multipolymer acrylic resin solution manufactured by Monsanto is an effective non-toxic adhesive is this application.

Figure 4:
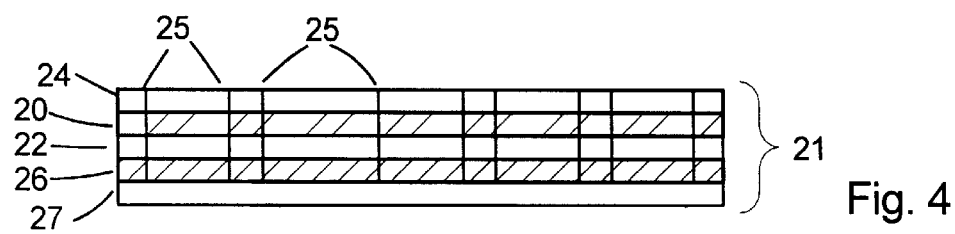
FIGS. 4 and 5 illustrate one method of how the reflecting film used in the present invention may be manufactured.
Figure 5:
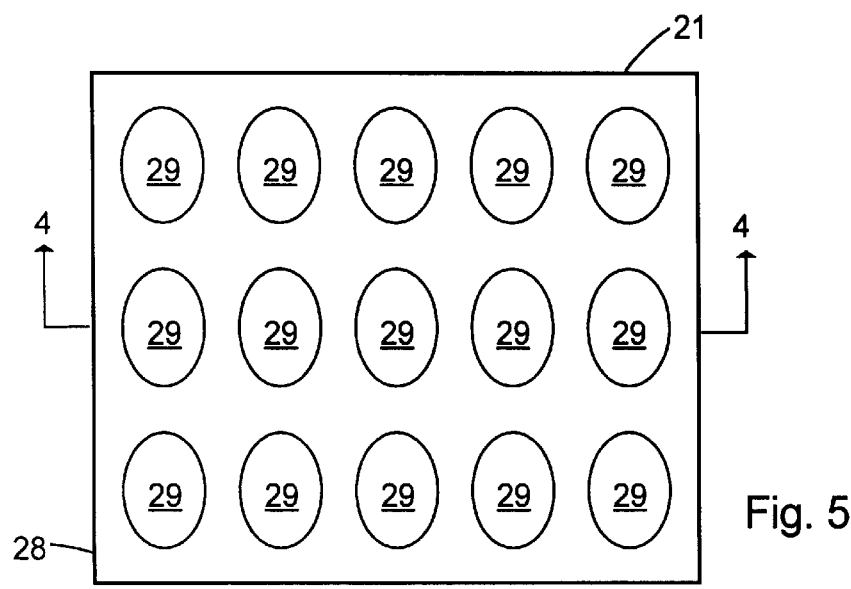

The individual mirrors formed of the reflective film may be made in the following way. Referring to FIGS. 4 and 5, a composite sheet 21 is formed from which the individual mirrors 29 are cut. First, a metallization layer 22 is formed on a sheet of plastic film 20. One suitable material for the plastic film 20 is 4-mil thick, type D Mylar plastic or a similar PET plastic material. The reflective metallization layer 22 may be made by fuming aluminum onto one surface of the plastic layer 20, so as to provide a reflective surface with an optical density of not less than 2.7.

The optional removable, protective ply 24 preferably consists of a 1 to 2-mil thick plastic sheet made of vinyl applied to the to the top, non-metallized surface of the composite sheet 21. Such protective films are kept in place by static adherence and are known in the art. This method provides a protective layer that is easily removed while eliminating the possibility of adhesive residue.

The bottom, metallized surface of plastic sheet 20 is coated with an adhesive layer 26. Preferably, this layer is an acrylic resin solution as described above or a similar adhesive. This adhesive may be used by applying it to the metallized plastic sheet material with a density of 6 to 8 pounds per 3000 square feet. The adhesive layer 26 is then covered with a release liner 27. This may be made of a 1-mil thick sheet of PET coated with a silicon release agent.

In FIG. 5, a composite sheet 28 is shown which has been fabricated as described above. Individual mirrors may be cut from sheet 28 and applied to individual blades 12 in the following manner. FIG. 5 shows a plurality of oblong reflective surfaces that have been formed from the sheet 28 by punching partway through the sheet. In particular, the peripheral cuts defining each mirror extend through the top four layers 24, 20, 22, and 26 of the composite sheet but do not extend through the release liner 27 on the bottom surface. This is shown by the cuts 25 in FIG. 4, which is a sectional view of the sheet shown in FIG. 5. Thus the sheet will consist of a plurality of individual reflective films, as shown in FIGS. 2 and 3, held together by the release liner 27.

These sheets may then be slit into strips one mirror wide and automatically applied to individual wooden blades 12 using readily available label-application machinery.

It should be appreciated that the reflecting film may be fabricated and applied to the blade by other methods while still providing a disposable dental mirror within the scope of the present invention.

Figure 6:
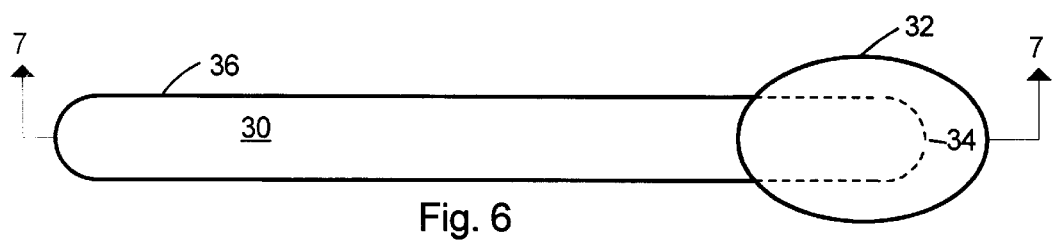
FIGS. 6 and 7 are top and sectional views respectively of a yet another embodiment of the present invention.
Figure 7:

FIGS. 6 and 7 are respectively top and sectional views of another embodiment of the invention. In FIGS. 6 and 7, a wooden handle 30 is comprised of a thin wooden blade similar to the wooden blade 12 of the FIGS. 2 and 3 embodiment. Attached to the distal end of the handle 30 is a mirror assembly 32 which provides the reflecting surface of the disposable mirror.

Referring to FIG. 7, the mirror assembly 32 includes a thin, flat, substrate 34 intermediate a metallized plastic film 18 and the handle portion 18. Substrate 34 is made of a relatively rigid material and serves to provide a flat surface on which the reflecting film 18 may be mounted. Especially in extreme environmental conditions, the substrate 34 tends to maintain a flatter surface than the wooden blade for mounting the reflective film 18, and thus tends to reduce or eliminate resulting distortion. Substrate 34 is preferably on the order of 0.015 to 0.040 inches thick and may be made of a plastic, such as PETG or polycarbonate, or of other materials having the desired properties. The substrate 34 is attached to the handle 30 with an adhesive layer, not shown in FIG. 7.

The mirror assembly 32 for the embodiment shown in FIGS. 6 and 7 may be manufactured by first producing a composite sheet 28 of reflective film 18, as described above. After the composite sheet 28 is completed, the adhesive layer 26 is applied to the top surface of a sheet of the material used for the rigid substrate 34. Release liner 27 may or may not be necessary depending on the particular details of the manufacturing operations used. Individual mirrors are then stamped out of the resulting composite sheet.

While handle 30 may be formed in the same way as described for FIGS. 2 and 3, with a head portion wider than handle portion, this is not necessary due to the addition of the rigid substrate 34. Thus, handle 30 may be made with a relatively uniform width along its length, as shown by the dotted lines 34 in FIG. 6, which reduces material wastage in making the handles and eliminates the need to properly orient the handle lengthwise in automated assembly operations. With the construction of FIGS. 6 and 7, impregnating the handle with a material such as carnauba wax to prevent absorption of moisture is less important, although still desirable. To attach the mirror assembly 32 to the handle, when impregnated with carnauba wax, the above described acrylic resin type of adhesive may be used, or alternatively, the mirror assembly may be attached with ethyl vinyl acetate in the form of a hot melt adhesive. Otherwise, the mirror assembly 32 may be mounted to handle 30 with any of a wide selection of non-toxic adhesives which are adherent to both wood and the material chosen for the substrate 34.

The planar configuration of the disposable dental mirror of the present invention allows a second reflecting surface to be usefully attached to the mirror. This configuration is especially advantageous in air abrasive dentistry, since by flipping the mirror, a dentist may quickly bring a new reflective surface to the work area without having to interrupt the procedure to get a new mirror after the first mirror becomes unusable. In conventional dental mirrors having a reflecting surface attached at an angle to the handle, a second reflecting surface on the back side of the mirror would rarely be usable.

Figure 8:
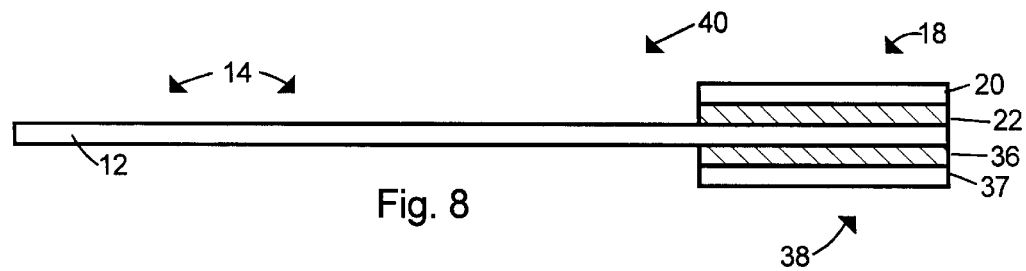
FIG. 8 shows a variation of the embodiment of FIGS. 2 and 3 in which reflecting surfaces are mounted on both sides of the blades.

For example, in FIG. 8 a dental mirror 40 similar in configuration to that shown in FIGS. 2 and 3 is shown in side elevation. As in FIGS. 2 and 3, mirror 40 has one reflective film 18 attached to one surface thereof. Additionally, a second reflective film 38 comprising metallization layer 36 and plastic layer 37 is attached to the opposite side of the blade 12 to provide a second reflective surface.

Similarly, in the embodiment shown in FIGS. 6 and 7, a second mirror assembly similar or identical to the first mirror assembly 32 shown in FIGS. 6 and 7 may be attached to the bottom surface 42 of the handle portion 30, as shown by dashed lines 43.

Figure 9:
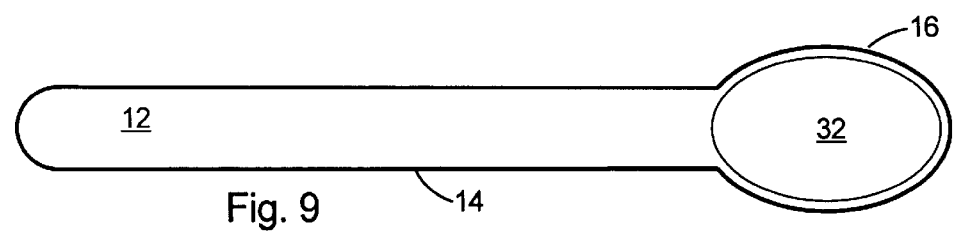
FIGS. 9 and 10 show yet another double-sided embodiment of the mirror configuration of FIGS. 2 and 3.
Figure 10:
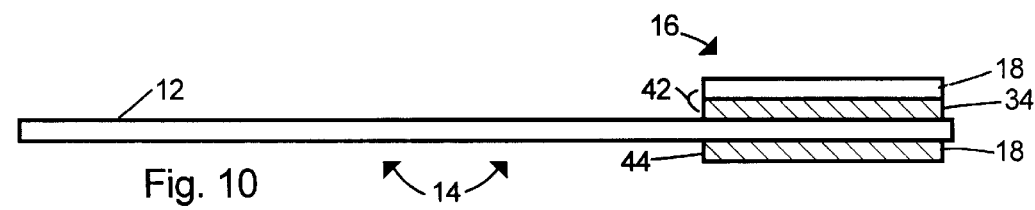

An alternate embodiment for a double-sided disposable dental mirror is shown in FIGS. 9 and 10. In these figures, a wooden blade portion 12 is provided which has a wider, oval-shaped head portion 16 and a narrower handle portion 14, similar in shape to the mirror of FIGS. 2 and 3. On the top surface is a first mirror 42 similar in construction to the mirror assembly 32 shown in FIG. 7. Thus, the mirror 42 includes a rigid substrate 34 to which is attached a reflecting film 18 made of metallized plastic film or similar material. As before, the rigid substrate 34 may be made of a plastic material and serves to counter any tendency of the blade to warp, thus providing a flat surface on which the reflective film 18 may be mounted.

On the bottom surface of the head portion 16 of the wooden blade is attached a second mirror 44 made up of a second reflecting film 44. The second mirror 44 is attached directly to the blade 12 without an intermediate substrate. The rigid substrate 34 attached to the top surface of the blade will serve to keep the head portion of the wooden blade flat, and accordingly the second mirror 44 does not need to include a rigid substrate.

There has been described a new and useful construction for a disposable dental mirror and a method of making the same. While the advantages of the present invention have been explained with reference to the exemplary embodiments described above, it should be appreciated that modifications to these embodiments will be made by those of ordinary skill in the art in applying the teachings of the invention to different situations and applications. Accordingly, the present invention should not be limited by the embodiments described above, but rather the scope of the invention should be interpreted only in accordance with the following claims.

What is claimed is:

1. A disposable dental mirror comprising:
   a handle in the form of a flat, elongated blade of substantially equal thickness along its length and having distal and proximal ends and top and bottom surfaces;
   a flexible, plastic, reflective film on the top surface of the blade at the distal end thereof to provide a substantially flat reflective surface; and
   the reflective film being attached directly to the blade top surface by means of an adhesive.

2. The mirror of claim 1 wherein the reflective material includes a metallized plastic film.

3. The mirror of claim 1 wherein the handle is made of wood.

4. The mirror of claim 1 wherein the handle is made of plastic.

5. The mirror of claim 1 wherein the reflective surface is provided by a plastic film having two surfaces and which is metallized on the first surface, the metallized surface being attached to the blade top surface by the adhesive.

6. The mirror of claim 5 wherein the flat elongated blade is made of wood.

7. The mirror of claim 3 wherein the wood blade includes means for preventing absorption of moisture by the wood.

8. The mirror of claim 7 wherein the means for preventing absorption includes a hydrophobic material which is applied to all surfaces of the wood blade.

9. The mirror of claim 8 wherein the means for preventing absorption includes carnauba wax.

10. The mirror of claim 9 wherein the adhesive material comprises an adhesive taken from the group including acrylic resin and ethyl vinyl acetate.

11. The mirror of claim 1 wherein the reflective film extends for a distance along the length of the top surface of the blade that is larger than the width of the blade.

12. The mirror of claim 11 wherein the reflective surface is oval in shape.

13. The mirror of claim 12 wherein the proximal portion of the blade is narrower than the distal end to provide a proximal portion adapted to be manually manipulated.

14. A disposable dental mirror comprising:
   a handle in the form of a flat, elongated blade made of wood, being of substantially equal thickness along its length, and having distal and proximal ends and top and bottom surfaces;
   a thin, flat, planar, substrate, made of a rigid material and having top and bottom surfaces;
   a flexible, plastic, reflective film covering substantially the entire top surface of the substrate and attached thereto to provide a mirror assembly having a flat reflective surface;
   means for attaching the substrate bottom surface to the top surface of the handle at the distal end thereof.

15. The mirror of claim 14 wherein the substrate is made of plastic.

16. The mirror of claim 15 wherein the reflective film comprises a metallized plastic film.

17. The mirror of claim 16 wherein the reflective film is provided by a plastic film having two surfaces and which is metallized on the first surface, the metallized surface being attached to the substrate top surface.

18. A method of manufacturing a disposable dental mirror including the steps of:
   shaping a flat, elongated blade of substantially equal thickness along its length and having distal and proximal ends and top and bottom surfaces to provide a head portion at the distal end and a handle portion at the proximal end with the handle portion being longer and narrower than the head portion and the head portion being of a rounded configuration about its periphery to eliminate sharp corners; and
   attaching a flexible, plastic reflective film to the top surface of the blade at the distal end thereof to provide a substantially flat reflective surface.

19. The method of claim 18 wherein the step of attaching includes the steps of:
   applying a metallization layer to one side of a thin sheet of transparent plastic film;
   applying a piece of the metallized plastic film to one surface of said head portion with the metallization layer adjacent to the blade and the plastic sheet away from the blade.

20. The method of claim 19 wherein the flat blade is made of wood, and further including the step of tumbling a plurality of blades together after the preparing step to smooth the edges thereof prior to attaching the reflective film.

21. The method of claim 20 wherein the step of tumbling includes the step of applying a hydrophobic material to the wooden handle.

22. The method of claim 20 wherein the step of tumbling includes the step of adding carnauba wax to the blades during the tumbling step.

23. A method of manufacturing the disposable dental mirror of claim 1, including the steps of:
   preparing a composite sheet from which a plurality of reflective surfaces will be formed, by:
      preparing a first sheet made of a flexible plastic reflective film;
      applying a layer of an adhesive to one surface of the first sheet; and
      applying a second sheet comprising a release liner over the layer of adhesive;
   punching a plurality of reflective surfaces out of the composite sheet; and
   removing individual reflective surfaces from the release liner and applying each reflective surface to the top surface of a handle at the distal end thereof so that the reflective surface is attached to the handle by the adhesive.

24. The method of claim 23 wherein the step of forming a composite sheet further includes the step of applying a third sheet of a thin flexible material to the surface of the first sheet opposite the adhesive layer to provide a protective layer over the reflective surface.

25. The method of claim 24 wherein the step of punching includes the step of cutting through the first and third sheets but not through the release liner to so that the composite sheet has a plurality of individual multiple reflective surfaces held in place by the release liner, whereby the individual reflective surfaces may be removed from the composite sheet and applied to individual handles by means of automated equipment.

* * * * *

UNITED STATES PATENT AND TRADEMARK OFFICE
CERTIFICATE OF CORRECTION

PATENT NO. : 6,142,777　　　　　　　　　　　　　　　　　　　Page 1 of 1
DATED : November 7, 2000
INVENTOR(S) : Paul E. Winston et al.

It is certified that error appears in the above-identified patent and that said Letters Patent is hereby corrected as shown below:

Title page,
ABSTRACT, lines 5 and 6, change "a one" to -- one --.

Column 4,
Line 50, change "to splinter of commonly" to -- to splinter. Of commonly --.

Column 8,
Line 8, delete "material" from the first line of claim 10.
Line 37, change "the first" to -- one -- in the third line of claim 17.

References Cited, U.S. PATENT DOCUMENTS,
The following references should be added:

| | | | |
|---|---|---|---|
| D281,718 | 12/1985 | Holstad | D24/139 |
| D329,899 | 9/1992 | Rihani | D24/139 |
| D348,515 | 7/1994 | Mangione | D24/139 |
| 3,711,176 | 1/1973 | Alfrey, Jr. | 359/359 |
| 3,829,199 | 8/1974 | Brown | 359/882 |
| 5,052,925 | 10/1991 | Stalcup | 433/30 |
| 5,655,904 | 8/1997 | Usul | 433/30 |

Signed and Sealed this

Nineteenth Day of March, 2002

*Attest:*

JAMES E. ROGAN
*Attesting Officer*　　　Director of the United States Patent and Trademark Office